United States Patent
Kato et al.

(10) Patent No.: US 8,946,480 B2
(45) Date of Patent: Feb. 3, 2015

(54) LIQUID CRYSTALLINE COMPOUND AND ELECTROLYTE MATERIAL

(71) Applicant: Japan Science and Technology Agency, Kawaguchi-shi, Saitama (JP)

(72) Inventors: Takashi Kato, Tokyo (JP); Masafumi Yoshio, Tokyo (JP); Bartolome Soberats, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 0 days.

(21) Appl. No.: 14/365,149

(22) PCT Filed: Dec. 13, 2012

(86) PCT No.: PCT/JP2012/082315
§ 371 (c)(1),
(2) Date: Jun. 13, 2014

(87) PCT Pub. No.: WO2013/089174
PCT Pub. Date: Jun. 20, 2013

(65) Prior Publication Data
US 2014/0336414 A1    Nov. 13, 2014

(30) Foreign Application Priority Data
Dec. 16, 2011    (JP) .................................. 2011-276146

(51) Int. Cl.
| | | |
|---|---|---|
| C07C 213/00 | (2006.01) | |
| C07C 215/00 | (2006.01) | |
| H01M 10/0566 | (2010.01) | |
| C07C 217/84 | (2006.01) | |
| H01M 10/0525 | (2010.01) | |

(52) U.S. Cl.
CPC ......... *H01M 10/0566* (2013.01); *C07C 217/84* (2013.01); *H01M 10/0525* (2013.01); *C07B 2200/13* (2013.01); *H01M 2300/0025* (2013.01)
USPC ........................................................ 564/287

(58) Field of Classification Search
None
See application file for complete search history.

(56) References Cited

FOREIGN PATENT DOCUMENTS

| | | |
|---|---|---|
| JP | 2001-338689 A | 12/2001 |
| JP | 2001-351435 A | 12/2001 |
| JP | 2008-037823 A | 2/2008 |
| JP | 2010-060973 A | 3/2010 |
| JP | 2011-192611 A | 9/2011 |
| WO | 2010/092897 A1 | 8/2010 |

OTHER PUBLICATIONS

Xu et al. (Chemical Communications, 2009, (43), 6634).*

(Continued)

*Primary Examiner* — Rosalynd Keys
*Assistant Examiner* — Jennifer C Sawyer

(57) ABSTRACT

A liquid crystalline compound and an electrolyte material in which the conductivity switches between ion conductivity and non-ion conductivity depending on changes in temperature, and thus a switching function can be obtained are proposed. The liquid crystalline compound has a columnar liquid crystal phase in which an ammonium group is linked with an alkoxyphenyl group. A structural change thereof occurs depending on changes in temperature, and the conductivity switches between ion-conducting and non-ion-conducting, and thus the switching function can be obtained.

10 Claims, 3 Drawing Sheets

(56) References Cited

OTHER PUBLICATIONS

Wikipedia, the free encyclopedia, "Lithium-Ion Secondary Battery," retrieved on Dec. 14, 2011, from the internet website <http://ja.wikipedia.org/wiki/%E3%83%AA%E3%83%81%E3%82%A6%E3%83%A0%E3%82%A4%E3%82%AA%E3%83%B3%E4%BA%8C%E6%AC%A1%E9%9B%BB%E6%B1%A0>.

International Search Report issued in PCT/JP2012/082315 and mailed on Mar. 5, 2013.

* cited by examiner

LIQUID CRYSTALLINE COMPOUND AND ELECTROLYTE MATERIAL

CROSS REFERENCE TO RELATED APPLICATIONS

This patent application is a U.S. national stage application under 35 U.S.C. §371 of International Patent Application No. PCT/JP2012/082315 filed on Dec. 13, 2012, which claims the benefit of foreign priority to Japanese Patent Application No. JP 2011-276146 filed on Dec. 16, 2011, the disclosures of all of which are hereby incorporated by reference in their entireties. The International Application was published in Japanese on Jun. 20, 2013, as International Publication No. WO 2013/089174 A1 under PCT Article 21(2).

TECHNICAL FIELD

The present invention relates to a liquid crystalline compound and an electrolyte material.

BACKGROUND ART

In recent years, as an electrolyte material used in a lithium ion secondary battery or the like, a solution composed of carbonate compounds that are volatile liquid and a lithium salt as a support salt is used (for example, refer to NPL 1).

CITATION LIST

Non-Patent Literature

[NPL 1] Wikipedia, free encyclopedia "lithium ion secondary battery", retrieved in Dec. 14, 2011, Internet, <URL: http://ja.wikipedia.org/wiki%E3%83%AA%E3%83%81%E3%82%A6%E3%83%A0%E3%82%A4%E3%82%AA%E3%83%B3%E4%BA%8C%E6%AC%A1%E9%9B%BB%E6%B1%A0

SUMMARY OF INVENTION

Technical Problem

Such an electrolyte material itself does not switch from a structure having ion conductivity to a structure having non-ion conductivity or from a structure having non-ion conductivity to a structure having ion conductivity. However, for a next-generation energy device element of the future based on a completely new idea as never before, there is also a need that, for example, the electrolyte material itself is capable of exhibiting a switching function between ion conductivity and non-ion conductivity due to external stimulation.

Therefore, the present invention has been taken into consideration in view of the above, and an object thereof is to provide a liquid crystalline compound and an electrolyte material in which the conductivity switches between ion conductivity and non-ion conductivity depending on the temperature, and thus the switching function can be obtained.

Solution to Problem

To solve the problem above, a liquid crystalline compound according to claim 1 of the present invention is represented by the following general formula,

[Chem. 2]

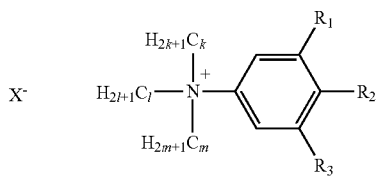

in which $R_1$, $R_2$, and $R_3$ in the formula are any of $R_1=R_2=R_3=O(CH_2)_{n-1}CH_3$ or $O(CH_2)_{q-1}(CF_2)_{p-1}CF_3$, $R_1=R_3=O(CH_2)_{n-1}CH_3$ or $O(CH_2)_{q-1}(CF_2)_{p-1}CF_3$ and $R_2=H$, and $R_1=R_2=O(CH_2)_{n-1}CH_3$ or $O(CH_2)_{q-1}(CF_2)_{p-1}CF_3$ and $R_3=H$, in which k, l, and m=1 to 18, n=6 to 18, q=1 to 5, and p=6 to 18, and in which $X^-$ is any of $BF_4^-$, $PF_6^-$, $CF_3SO_3^-$, $(CF_3SO_2)_2N^-$, $CH_3SO_3^-$, $CH_3COO^-$, $CF_3COO^-$, $ClO_4^-$, $Br^-$, $I^-$, $Cl^-$, or $F^-$.

In addition, an electrolyte material according to claim 5 includes the liquid crystalline compound according to any one of claims 1 to 4, in which a phase transition of the liquid crystalline compound occurs depending on the temperature and the conductivity switches from ion conductivity to non-ion conductivity or from non-ion conductivity to ion conductivity.

Advantageous Effects of Invention

According to claims 1 and 5 of the present invention, a liquid crystalline compound and an electrolyte material in which the conductivity switches between ion conductivity and non-ion conductivity depending on the temperature, and thus the switching function of conductivity can be obtained, can be provided.

DESCRIPTION OF EMBODIMENTS

Figure 1:
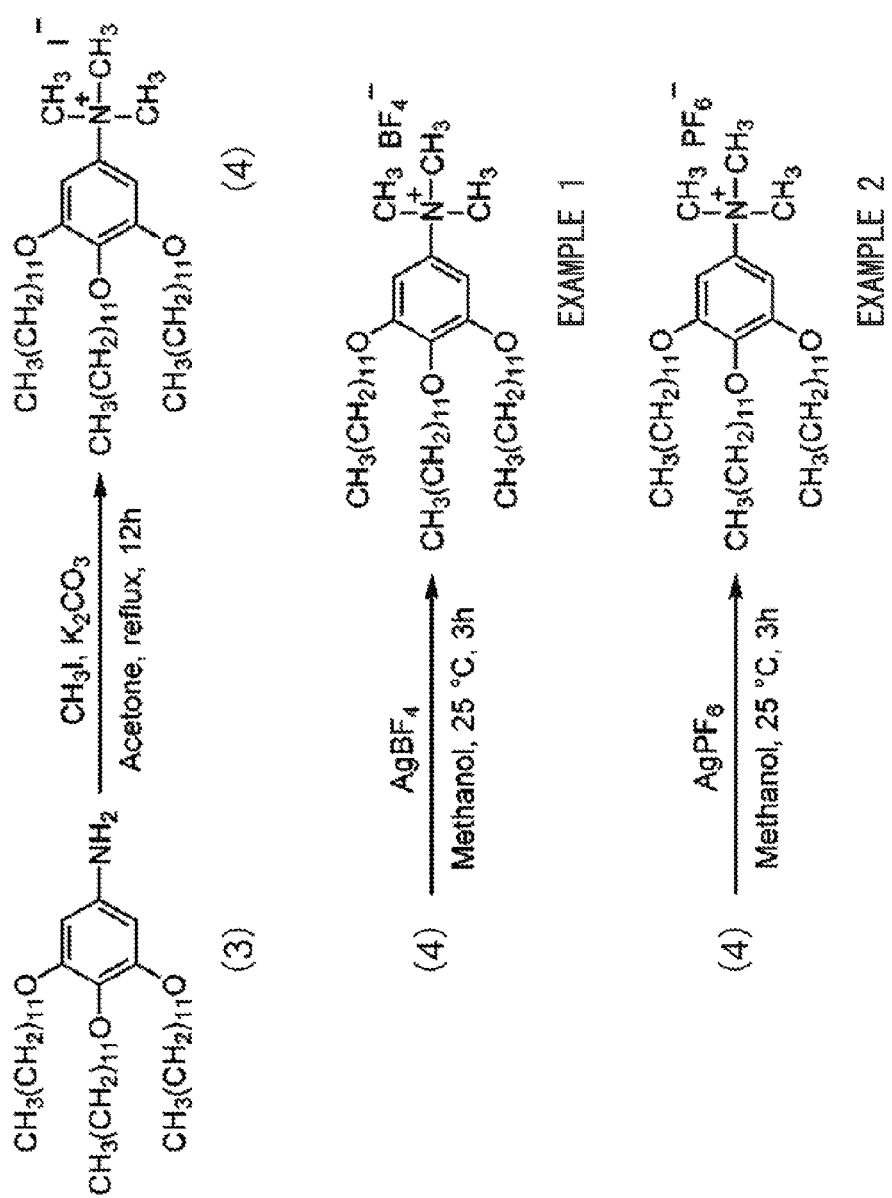
FIG. 1 is a diagram showing a synthesis scheme of a liquid crystalline compound of Example 1 and Example 2.

Hereinafter, embodiments of the present invention will be described in detail with reference to drawings.

(1) Configuration of Liquid Crystalline Compound of the Present Invention

A liquid crystalline compound of the present invention consists of an ammonium group linked with an alkoxyphenyl group and the compound exhibits columnar (Col) liquid crystalline phases. The structural change is induced by the change in temperature, and thus ionic conductive characteristics can changes. Specifically, the liquid crystalline compound of the present invention is represented by the following general formula.

[Chem. 3]

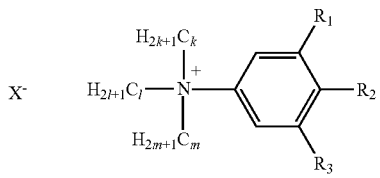

Here, $R_1$, $R_2$, and $R_3$ in the formula of Chem. 3 described above are any of the following three forms. Firstly, $R_1$, $R_2$, and $R_3$ all consist of the same group and $R_1=R_2=R_3=O(CH_2)_{n-1}CH_3$ or $O(CH_2)_{q-1}(CF_2)_{p-1}CF_3$. Secondly, $R_1$ and $R_3$ consist of the same group, $R_1=R_3=O(CH_2)_{n-1}CH_3$ or $O(CH_2)_{q-1}(CF_2)_{p-1}CF_3$, and $R_2=H$. Thirdly, $R_1$ and $R_2$ consist of the same group, $R_1=R_2=O(CH_2)_{64}—CH_3$ or $O(CH_2)_{q-1}(CF_2)_{p-1}CF_3$, and $R_3=H$.

In addition, in any of these three forms, k, l, and m=1 to 18, n=6 to 18, q=1 to 5, and p=6 to 18. $X^-$ represents a monovalent anion and is any of $BF_4^-$, $PF_6^-$, $CF_3SO_3^-$, $(CF_3SO_2)_2N^-$, $CH_3SO_3^-$, $CH_3COO^-$, $CF_3COO^-$, $ClO_4^-$, $Br^-$, $I^-$, $Cl^-$, or $F^-$.

The liquid crystalline compound represented by such a general formula forms a liquid crystalline phase having non-ion conductivity in which ions cannot move at a low temperature and forms a liquid crystalline phase having ion conductivity in which ions are capable of moving at a high temperature, and a phase transition of the liquid crystalline phases occurs depending on the temperature. In addition, the liquid crystalline compound of the present invention is formed so that the conductivity of the liquid crystalline phases repeatedly changes from ion-conducting to non-ion-conducting or from non-ion-conducting to ion-conducting, depending on the temperature, and thus the switching function can be obtained.

In fact, the liquid crystalline compound forms a rectangular columnar structure at a low temperature and a rectangular columnar phase which is not ion conductive is formed. On the other hand, the structure of the liquid crystalline compound changes to a hexagonal columnar structure when the low temperature state thereof changes to a high temperature state by heating and a phase transition occurs to a hexagonal columnar phase which is ion conductive. The positional relation between an anion and a cation in the structure is changed due to the structure change to the hexagonal columnar structure, and then the anion can move freely in the hexagonal columnar structure. Moreover, when this liquid crystalline compound in hexagonal columnar structure is further heated up to a higher temperature, a liquid crystal state of the liquid crystalline compound can change to a liquid state.

For such a liquid crystalline compound, the phase transition temperature at which the switching between ion-conducting and non-conducting states occurs can be lowered by reducing the number of $CH_2$ and $CF_2$ by making n, q, and p smaller, and thus shortening the length of $R_1$, $R_2$, and $R_3$ in the general formula of Chem. 3 described above. Therefore, when this liquid crystalline compound is used in various kinds of switching materials which require the switching function between ion conductivity and non-ion conductivity at the low temperature state, the liquid crystalline compound which is suitable for these switching materials can be obtained by appropriately shortening the length of $R_1$, $R_2$, and $R_3$ in the liquid crystalline compound.

Furthermore, when $R_1$, $R_2$, and $R_3$ are set to $O(CH_2)_{q-1}(CF_2)_{p-1}CF_3$ including fluorine in the liquid crystalline compound, the strength of the liquid crystal structure can be improved, compared to the liquid crystalline compound in which $R_1$, $R_2$, and $R_3$ are set to $O(CH_2)_{n-1}CH_3$. Here, in a case where $CF_3SO_3^-$ or $(CF_3SO_2)_2N$ is used as $X^-$, an anion becomes bigger; however, even in this case, the structure can become stabilized without being affected by an anion of $CF_3SO_3^-$ or $(CF_3SO_2)_2N$ and high ion conductivity can be realized if $R_1$, $R_2$, and $R_3$ are set to $O(CH_2)_{q-1}(CF_2)_{p-1}CF_3$.

(2) Specific Liquid Crystalline Compound of the Present Invention (2-1) Liquid Crystalline Compound in Example 1

Here, a liquid crystalline compound represented by the following general formula shows an example of the liquid crystalline compound represented by the general formula in Chem. 3 described above.

[Chem. 4]

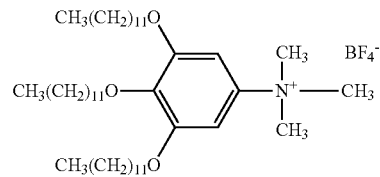

In this case, in the liquid crystalline compound represented by the general formula in Chem. 4 described above, which is used in Example 1, n is set to 12 and thus $R_1=R_2=R_3=O(CH_2)_{11}CH_3$ is set; k, l, and m is set to 1; and $X^-$ is set to $BF_4^-$ in the formula of Chem. 3. This liquid crystalline compound in Example 1 can form the rectangular columnar structure having non-ion conductivity when in a low temperature state which is from 44° C. to 122° C., and the liquid crystalline compound can form the hexagonal columnar structure having ion conductivity when in a high temperature state which is 141° C. or higher and lower than 196° C., which is higher than the low temperature state. Moreover, in a case where the temperature is set to 196° C. or higher, the liquid crystalline compound changes from a liquid crystal to a liquid. In addition, as to the liquid crystalline compound in Example 1, when the temperature is lowered from a high temperature to a low temperature, the structure changes from the hexagonal columnar structure to the rectangular columnar structure, and conversely, when the temperature is raised from a low temperature to a high temperature, the structure changes again from the rectangular columnar structure to the hexagonal columnar structure. In this manner, the liquid crystalline compound in Example 1 has switching characteristics in which the structure thereof changes repeatedly depending on the temperature due to cooling and heating, and ion conductivity and non-ion conductivity arbitrarily switch.

(2-2) Liquid Crystalline Compound in Example 2

In addition, a liquid crystalline compound represented by the following general formula is also an example of the liquid crystalline compound represented by the general formula in Chem. 3 described above.

[Chem. 5]

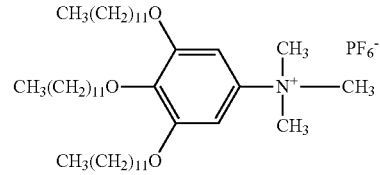

In this case, in the liquid crystalline compound represented by the general formula in Chem. 5 described above, which is used in Example 2, n is set to 12 and thus $R_1$=$R_2$=$R_3$=O(CH$_2$)$_{11}$CH$_3$ is set; k, l, and m is set to 1; and X$^-$ is set to PF$_6^-$ in the formula of Chem. 3. This liquid crystalline compound in Example 2 can form a rectangular columnar structure having non-ion conductivity when in a low temperature state which is from 54° C. to 117° C., and the liquid crystalline compound can form a hexagonal columnar structure having ion conductivity when in a high temperature state which is 122° C. or higher and lower than 168° C., which is higher than the low temperature state. Moreover, in a case where the temperature is set to 168° C. or higher, the liquid crystalline compound changes from a liquid crystal to a liquid. In addition, for the liquid crystalline compound in Example 2, when the temperature is lowered from a high temperature to a low temperature, the structure changes from the hexagonal columnar structure to the rectangular columnar structure, and conversely, when the temperature is raised from a low temperature to a high temperature, the structure changes again from the rectangular columnar structure to the hexagonal columnar. In this manner, the liquid crystalline compound in Example 2 has switching characteristics in which the structure thereof is repeatedly changed depending on changes in temperature due to cooling and heating, and ion conductivity and non-ion conductivity arbitrarily switch.

(3) Synthesis Scheme of Liquid Crystalline Compound of Example 1 and Example 2

Next, a synthetic scheme of above-mentioned each liquid crystalline compound used in Example 1 and Example 2 will be described. These liquid crystalline compounds used in Example 1 and Example 2 can be synthesized by a synthetic scheme shown in FIG. 1. Moreover, here, a synthetic scheme of the liquid crystalline compounds in Example 1 and Example 2 in brief will be provided and a detailed explanation will be provided later in "(5) Synthesis of liquid crystalline compound".

In this case, a compound represented by the general formula (3) in FIG. 1 is used as a starting material, an ammonium group is introduced into this compound, and a precursor represented by the general formula (4) is synthesized. Moreover, here, the compound represented by the general formula (3) can be synthesized in accordance with the literature "V. Percec, E. Aqad, M. Peterca, J. G. Rudick, L. Lemon, J. C. Ronda, B. B. De, P. A. Heiney, and E. W. Meijer, "Steric Communication of Chiral Information Observed in Dendronized Polyacetylenes", Journal of the American Chemical Society, 2006, 128, 16365-16372".

Hereinafter, a description will be provided of a case of synthesizing the liquid crystalline compounds used in Example 1 and Example 2 in which $R_1$, $R_2$, and $R_3$ are set to O(CH$_2$)$_{11}$CH$_3$; however, for example, in a case of synthesizing the liquid crystalline compound in which $R_1$, $R_2$, and $R_3$ are set to O(CH$_2$)$_{q-1}$(CF$_2$)$_{p-1}$CF$_3$, a compound having O(CH$_2$)$_{q-1}$(CF$_2$)$_{p-1}$CF$_3$ instead of O(CH$_2$)$_{11}$CH$_3$ is used as a starting material. In this manner, regarding $R_1$, $R_2$, and $R_3$ in the general formula of Chem. 3, it is possible to synthesize the liquid crystalline compound having desired $R_1$, $R_2$, and $R_3$ by using a starting material having desired $R_1$, $R_2$, and $R_3$.

Then, each liquid crystalline compound used in Example 1 and Example 2 and another liquid crystalline compound represented by the general formula in Chem. 3 described above can be synthesized by introducing a silver compound such as AgBF$_4$ or AgPF$_6$ containing the desired anion such as BF$_4^-$ or PF$_6^-$ into the synthesized precursor represented by the general formula (4) to exchange an anion in the precursor with the desired anion, or the like.

(4) Action and Effect

In to the above configuration, the structural change occurs depending on the temperature due to the structure of this liquid crystalline compound being formed by the general formula represented by Chem. 3 described above, and thus the liquid crystalline compound exhibits a switching property to switch the physical property between ion conductivity and non-ion conductivity.

Specifically, in this liquid crystalline compound, the liquid crystalline phase becomes the rectangular columnar phase and non-ion-conductive at a low temperature in which an anion cannot move, and on the other hand, the liquid crystalline phase becomes a hexagonal columnar phase and ion-conductive at a high temperature in which an anion can move. Since such a switching function in which ionic conductive characteristics are switched repeatedly depending on each change in temperature from a high temperature to a low temperature or from a low temperature to a high temperature is exhibited, it is possible to use the liquid crystalline compound of the present invention as a switching material.

In addition, such a liquid crystalline compound can be used as an electrolyte material for various kinds of batteries such as a lithium ion secondary battery. In this case, the electrolyte material has a configuration containing the liquid crystalline compound of the present invention wherein the liquid crystalline compound is mixed with an ion conductive medium such as a lithium salt. In the electrolyte material, the liquid crystalline compound contains a lithium ion (an ion conductive medium) in its structure, the lithium ion moves during the hexagonal columnar phase having ion conductivity, and thus such an electrolyte material can function as an electrolyte.

In this case, the lithium ion secondary battery can be formed, and be provided with a switching function in which ion conductivity is turned on and off in the electrolyte material depending on changes in ambient temperature. Moreover, the case that a lithium ion is used as an ion conductive medium which is mixed with the liquid crystalline compound to obtain electrolyte material for a lithium ion secondary battery is described here; however, the present invention is not limited thereto, and it is possible to use an electrolyte material for other various kinds of batteries by mixing various other kinds of ion conductive media with the liquid crystalline compound.

Furthermore, this liquid crystalline compound can be also used as an electrolyte material in an electric double layer capacitor. Here, the electric double layer capacitor has a configuration in which an anode and a cathode are oppositely arranged from each other and separated by a predetermined distance, and has a configuration in which the anode and cathode are immersed into the electrolyte material containing the liquid crystalline compound of the present invention. In such an electric double layer capacitor, anions and cations are respectively attracted to the anode and the cathode during charging and an electric double layer is formed. The electric double layer capacitor in this charging state can be discharged by connecting a load to the anode and the cathode and by the temperature of the electrolyte material at which the electrolyte material has ion conductivity.

Furthermore, this liquid crystalline compound can be used as a switching material for a temperature sensor. In this case, the temperature sensor can recognize that the liquid crystalline compound in the switching material has reached the predetermined temperature by the energization due to the switch from non-ion conductivity to ion conductivity at the predetermined temperature.

In this manner, by using the liquid crystalline compound of the present invention as an electrolyte material, a switching material or the like for various kinds of devices driven by ion conduction, it is possible to give the switching function between ion conductivity and non-ion conductivity depending on the temperature to these various kinds of devices.

EXAMPLE (5) Synthesis of Liquid Crystalline Compound

Next, each liquid crystalline compound used in Example 1 and Example 2 described above was synthesized in accordance with the synthesis scheme shown in FIG. 1, and various kinds of verifications were performed for each liquid crystalline compound in Example 1 and Example 2. Here, after the precursor represented by the general formula (4) was synthesized, each liquid crystalline compound in Example 1 and Example 2 was synthesized using this precursor, as shown in FIG. 1.

(5-1) Synthesis of Precursor

First of all, the precursor used for the synthesis of each liquid crystalline compound of Example 1 and Example 2 was synthesized using the compound represented by the general formula (3). The compound represented by the general formula (3) as a staring material was synthesized in accordance with the literature "V. Percec, E. Aqad, M. Peterca, J. G Rudick, L. Lemon, J. C. Ronda, B. B. De, P. A. Heiney, and E. W. Meijer, "Steric Communication of Chiral Information Observed in Dendronized Polyacetylenes", Journal of the American Chemical Society, 2006, 128, 16365-16372".

Next, iodomethane (2.27 g, 16.9 mmol) and potassium carbonate (0.652 g, 4.7 mmol) were added to an acetone solution (30 ml) of the compound represented by the general formula (3) (0.61 g, 0.94 mmol), the solution was stirred for 12 hours while refluxing, and the reaction solution was obtained.

Next, this reaction solution was concentrated under reduced pressure by an evaporator, 20 ml of chloroform was added to a residual thereof, and an insoluble salt was removed by filtration. After that, the filtrate was concentrated, the residue was purified by silica gel chromatography (eluent: chloroform/methanol=95/5), and the precursor represented by the general formula (4) was obtained.

Furthermore, the recrystallization from a mixed solvent of ethyl acetate and methanol gave the precursor as a white solid in a yield of 74% (0.57 g, 0.7 mmol). The identification of the precursor of the general formula (4) was performed by $^1$H NMR, $^{13}$C NMR and MALDI-TOF MASS. $^1$H NMR (400 MHz, CDCl$_3$, δ): 6.97 (s, 2H; ArH), 4.12 (t, J=6.4 Hz, 4H; CH$_2$), 3.99-3.94 (m, 11H; CH$_2$; CH$_3$), 1.82 (m, 4H; CH$_2$), 1.72 (m, 2H; CH$_2$), 1.49-1.26 (m, 54H; CH$_2$), 0.89 (t, J=6.8 Hz, 9H; CH$_3$); $^{13}$C NMR (100 MHz, CDCl$_3$, δ): 153.93, 142.52, 139.49, 98.89, 73.63, 70.87, 57.85, 31.90, 30.24, 29.70, 29.63, 29.53, 29.44, 29.35, 29.27, 26.07, 26.00, 22.67, 14.10; MS (MALDI-TOF): [M−I]+calcd. For C$_{45}$H$_{86}$NO$_3$, 688.660. found, 688.296.

(5-2) Synthesis of Liquid Crystalline Compound of Example 1

Next, the liquid crystalline compound of Example 1 described above was synthesized from the precursor. In this case, a methanol solution (10 ml) of AgBF$_4$ (0.34 g, 1.76 mmol) was added dropwise to a methanol solution (30 ml) of the precursor (0.47 g, 0.58 mmol), the solution was stirred at 25° C. for 3 hours, and the reaction solution was obtained.

Next, the precipitate in the reaction solution was filtrated and the solvent was removed. The residue was purified by silica gel chromatography (eluent: chloroform/methanol=95/5) and recrystallized from a mixed solvent of ethyl acetate and methanol twice to give the liquid crystalline compound in Example 1 as a white solid in a yield of 77% (0.35 g, 0.45 mmol). The identification of the liquid crystalline compound in Example 1 was performed by $^1$H NMR, $^{13}$C NMR, MALDI-TOF MASS and an elemental analysis. $^1$H NMR (400 MHz, CDCl$_3$, δ): 6.84 (s, 2H; ArH), 4.05 (t, J=6.4 Hz, 4H; CH$_2$), 3.96 (t, J=6.4 Hz, 2H; CH$_2$), 3.66 (s, 9H; CH$_3$), 1.84 (m, 4H; CH$_2$), 1.80 (m, 2H; CH$_2$), 1.46 (m, 6H; CH$_2$), 1.26 (m, 48H; CH$_2$), 0.88 (t, J=6.8, 9H; CH$_3$); $^{13}$C NMR (100 MHz, CDCl$_3$, δ): 153.93, 141.98, 139.48, 98.32, 73.64, 70.03, 57.31, 31.91, 30.25, 29.74, 29.72, 29.68, 29.66, 24.64, 29.55, 29.42, 29.37, 29.28, 26.05, 26.02, 22.68, 14.10; MS (MALDI-TOF): [M−BF$_4$]+calcd. for C$_{45}$H$_{86}$NO$_3$, 688.661. found, 688.165; Elemental analysis calcd. for C$_{45}$H$_{86}$BF$_4$NO$_3$: C, 69.65; H, 11.17; N, 1.81. found: C, 69.49; H, 11.21; N, 2.05.

(5-3) Synthesis of Liquid Crystalline Compound in Example 2

Next, the liquid crystalline compound of Example 2 described above was synthesized from the precursor. In this case, a methanol solution (10 ml) of AgPF$_6$ (0.50 g, 1.98 mmol) was added dropwise to a methanol solution (30 ml) of the precursor (0.53 g, 0.66 mmol), and the solution was stirred at 25° C. for 3 hours.

Next, the precipitate in the reaction solution was filtrated and the solvent was evaporated. The residue was purified by silica gel chromatography (eluent:chloroform/methanol=95/5) and recrystallized from a mixed solvent of ethyl acetate and methanol twice to afford the liquid crystalline compound in Example 2 as a white solid in a yield of 49% (0.27 g, 0.32 mmol). The identification of the liquid crystalline compound in Example 2 was performed by $^1$H NMR, $^{13}$C NMR, MALDI-TOF MASS and an elemental analysis. $^1$H NMR (400 MHz, CDCl$_3$, δ): 6.79 (s, 2H; ArH), 4.04 (t, J=6.4 Hz, 4H; CH$_2$), 3.97 (t, J=6.4 Hz, 2H; CH$_2$), 3.62 (s, 9H; CH$_3$), 1.82 (m, 4H; CH$_2$), 1.73 (m, 2H; CH$_2$), 1.54 (m, 6H; CH$_2$), 1.26 (m, 48H; CH$_2$), 0.88 (t, J=6.4, 9H; CH$_3$); $^{13}$C NMR (100 MHz, CDCl$_3$, δ): 154.09, 141.72, 139.78, 98.22, 73.65, 70.05, 57.41, 31.81, 30.16, 29.60, 29.55, 29.52, 29.43, 29.29, 29.25, 29.17, 25.88, 22.56, 13.96; MS (MALDI-TOF): [M−PF$_6$]+ calcd. for C$_{45}$H$_{86}$NO$_3$, 688.661. found, 688.103; Elemental analysis calcd. for C$_{45}$H$_{86}$PF$_6$NO$_3$: C, 64.80; H, 10.39; N, 1.68. found: C, 64.88; H, 10.49; N, 1.88.

(5-4) Verification Result

For each liquid crystalline compound of Example 1 and Example 2, the thermal phase transition behavior was examined by differential scanning calorimetry and polarizing microscopic observation. As a result, for the liquid crystalline compound of Example 1, the crystal phase became a rectangular columnar phase at 44° C., became a hexagonal columnar phase at 141° C., and became a liquid phase at 196° C. In addition, for the liquid crystalline compound in Example 2, the crystal phase became a rectangular columnar phase at 54° C., became a hexagonal columnar phase at 122° C., and became the liquid phase at 168° C. Moreover, the identification of the liquid crystal structure of the liquid crystalline compounds of Example 1 and Example 2 was performed by a wide angle X-ray diffraction measurement.

Figure 2:
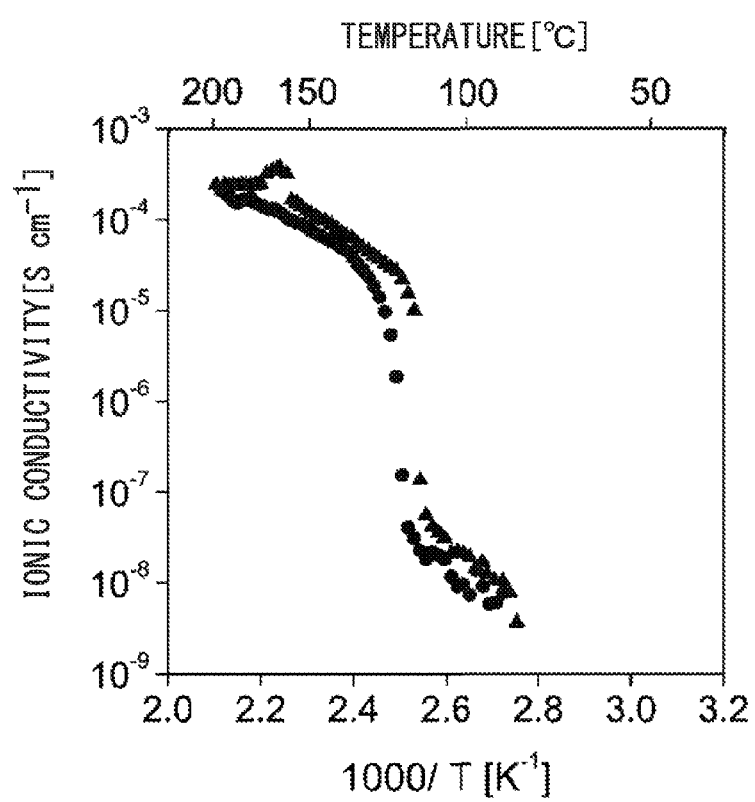
FIG. 2 is a graph showing temperature dependence of an ionic conductivity of Example 1 and Example 2.

Next, the temperature dependency of the ionic conductivity of each liquid crystalline compound of Example 1 and Example 2 was evaluated by an AC impedance measurement. The results are shown in FIG. 2. In FIG. 2, the liquid crystalline compound of Example 1 is indicated as ●, and the liquid crystalline compound of Example 2 is indicated as ▲. From these results, it was confirmed that the ionic conductivity of any liquid crystalline compounds of Example 1 and Example 2 rapidly increased from $10^{-8}$ Scm$^{-1}$ to $10^{-4}$ Scm$^{-1}$ during heating from 100° C. to 150° C. For this reason, it was confirmed that the liquid crystalline compounds of Example 1 and Example 2 exhibited the switching from non-conducting to conducting states by heating up to 150° C.

Figure 3:
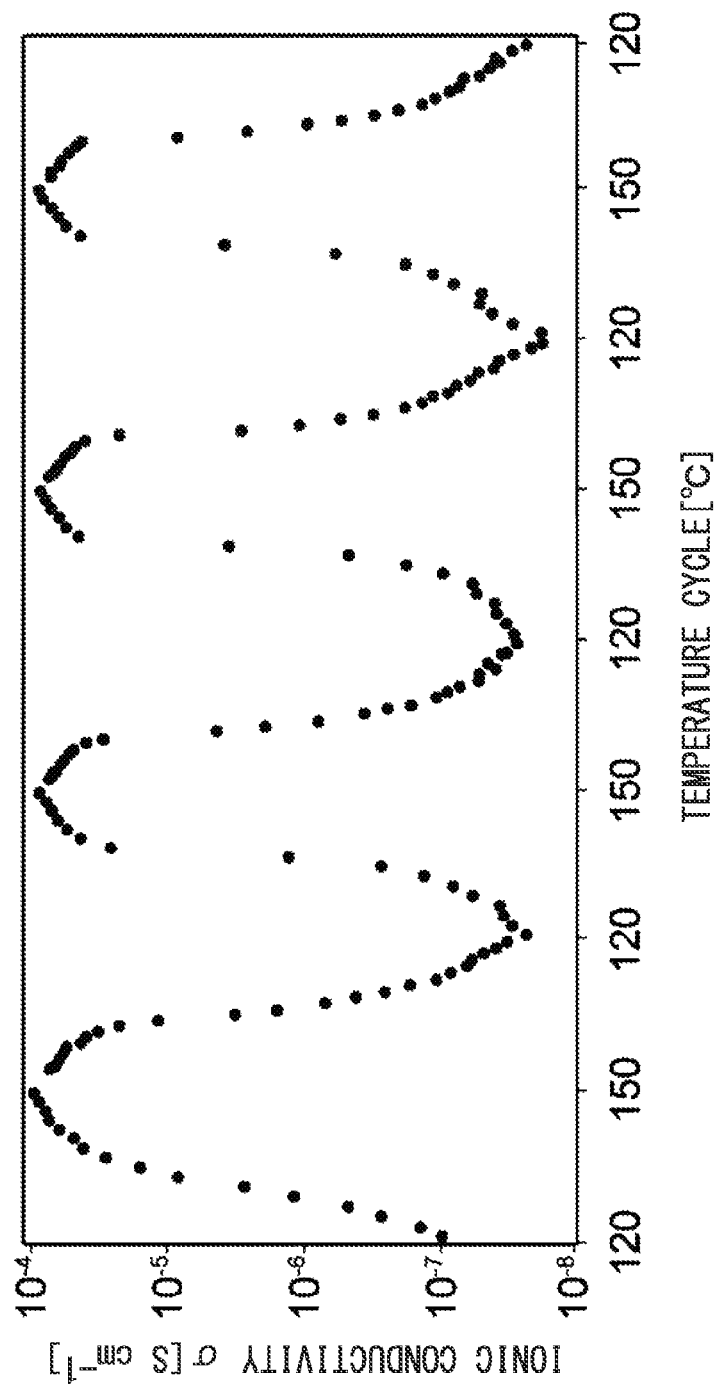
FIG. 3 is a graph showing temperature cycle characteristics of an ionic conductivity of Example 1.

In addition, for the liquid crystalline compound of Example 1, ionic conductive characteristics in a temperature raising process and in a cooling process were examined at a temperature cycle in which the temperature was raised up from 120° C. to 150° C., and then cooled from 150° C. and 120° C., and the results shown in FIG. 3 were obtained. From the results in FIG. 3, during four cycles of the temperature raising-cooling, excellent change in ionic conductive characteristics was exhibited and no decrease in ionic conductivity due to the deterioration of the liquid crystalline compound of Example 1 was seen. In this manner, for the liquid crystalline compound of Example 1, it is possible to confirm that the conductivity was repeatedly changed from ion conductivity to non-ion conductivity or also from non-ion conductivity to ion conductivity depending on the temperature, and thus the switching function was obtained (an off-state $10^{-8}$ Scm$^{-1}$, an on-state $10^{-4}$ Scm$^{-1}$).

Moreover, the present invention is not limited to the present embodiment and various modifications can be conducted within a range of the scope of the present invention. For example, the synthesis scheme of each liquid crystalline compound of Example 1 and Example 2 is not limited to the synthesis scheme shown in FIG. 1 and the liquid crystalline compound may be synthesized by various synthesis schemes.

The invention claimed is:

1. A liquid crystalline compound represented by the following general formula,

[Chem. 1]

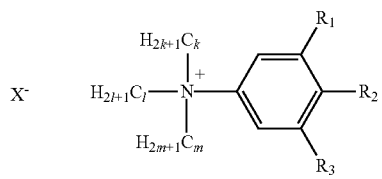

wherein $R_1$, $R_2$, and $R_3$ in the formula are any of
$R_1=R_2=R_3=O(CH_2)_{n-1}CH_3$ or $O(CH_2)_{q-1}(CF_2)_{p-1}CF_3$,
$R_1=R_3=O(CH_2)_{n-1}CH_3$ or $O(CH_2)_{q-1}(CF_2)_{p-1}CF_3$ and $R_2=H$, and
$R_1=R_2=O(CH_2)_{n-1}CH_3$ or $O(CH_2)_{q-1}(CF_2)_{p-1}CF_3$ and $R_3=H$;
wherein
k, l, and m=1 to 18,
n=6 to 18,
q=1 to 5, and
p=6 to 18; and
wherein X$^-$ is any of BF$_4^-$, PF$_6^-$, CF$_3$SO$_3^-$, (CF$_3$SO$_2$)$_2$N$^-$, CH$_3$SO$_3^-$, CH$_3$COO$^-$, CF$_3$COO$^-$, ClO$_4^-$, Br$^-$, I$^-$, Cl$^-$, or F$^-$.

2. The liquid crystalline compound according to claim 1, wherein a phase transition of liquid crystalline phases occurs from a rectangular columnar phase which is non-ion-conductive to a hexagonal columnar phase which is ion-conductive by heating.

3. The liquid crystalline compound according to claim 1, wherein a phase transition of liquid crystalline phases occurs from a hexagonal columnar phase which is ion-conductive to a rectangular columnar phase which is non-ion-conductive by lowering the temperature.

4. The liquid crystalline compound according to claim 2, wherein
an ionic conductivity reaches $10^{-4}$ Scm$^{-1}$ or more during the hexagonal columnar phase, and
an ionic conductivity reaches $10^{-8}$ Scm$^{-1}$ or less during the rectangular columnar phase.

5. An electrolyte material comprising:
the liquid crystalline compound according to claim 1,
wherein a phase transition of liquid crystalline phases of the liquid crystalline compound occurs depending on a change in temperature and a conductivity switches from ion-conducting to non-ion-conducting or from non-ion-conducting to ion-conducting.

6. The liquid crystalline compound according to claim 3, wherein
an ionic conductivity reaches $10^{-4}$ Scm$^{-1}$ or more during the hexagonal columnar phase, and
an ionic conductivity reaches $10^{-8}$ Scm$^{-1}$ or less during the rectangular columnar phase.

7. An electrolyte material comprising:
the liquid crystalline compound according to claim 2,
wherein a phase transition of liquid crystalline phases of the liquid crystalline compound occurs depending on a change in temperature and a conductivity switches from ion-conducting to non-ion-conducting or from non-ion-conducting to ion-conducting.

8. An electrolyte material comprising:
the liquid crystalline compound according to claim 3,
wherein a phase transition of liquid crystalline phases of the liquid crystalline compound occurs depending on a change in temperature and a conductivity switches from ion-conducting to non-ion-conducting or from non-ion-conducting to ion-conducting.

9. An electrolyte material comprising:
the liquid crystalline compound according to claim 4,
wherein a phase transition of liquid crystalline phases of the liquid crystalline compound occurs depending on a change in temperature and a conductivity switches from ion-conducting to non-ion-conducting or from non-ion-conducting to ion-conducting.

10. An electrolyte material comprising:
the liquid crystalline compound according to claim 6,
wherein a phase transition of liquid crystalline phases of the liquid crystalline compound occurs depending on a change in temperature and a conductivity switches from ion-conducting to non-ion-conducting or from non-ion-conducting to ion-conducting.

* * * * *